United States Patent [19]
Gasson

[11] Patent Number: 5,360,617
[45] Date of Patent: Nov. 1, 1994

[54] METHOD OF MAKING CHEESE USING VIRAL ENZYMES

[75] Inventor: Michael J. Gasson, Norwich, United Kingdom

[73] Assignee: Agricultural and Food Research Council, England

[21] Appl. No.: 668,523

[22] Filed: Mar. 13, 1991

Related U.S. Application Data

[63] Continuation of PCT/6B89/00791, Jul. 12, 1989, abandoned.

[30] Foreign Application Priority Data

Jul. 13, 1988 [GB] United Kingdom ............... 8816693.9

[51] Int. Cl.$^5$ ................................................ A23C 9/12
[52] U.S. Cl. ........................................ 426/36; 426/42; 426/582
[58] Field of Search ..................... 426/36, 38, 42, 43, 426/580, 582

[56] References Cited

U.S. PATENT DOCUMENTS

| | | | |
|---|---|---|---|
| 4,851,240 | 7/1989 | Day et al. | 426/53 |
| 4,959,229 | 9/1990 | Reddy et al. | 426/39 |
| 5,006,347 | 4/1991 | Day et al. | 426/36 |

OTHER PUBLICATIONS

Barbar Hohn, (1979) *Methods in Enzymology*, (ed., R. Wu)., vol. 68, 299–309.
Scalenghe, F., Turco, E., Edstrom, J. E. Pirrotta, V. & Melli, M. (1981). Chromosoma 82, 205–216.
Terzaghi, B.K. & Sandine, N.E. (1975). *Applied Microbiology*, 29:807–813.
Feirtag et al., J. Dairy Sci., "Dairy Foods Research Papers", 70:1773–1778 (1987).
Mullan et al., J. Dairy Research, "Lysin production by C2(W), a prolate phage for Streptoccus lactis C2", 52:113–121 (1985).
Mullan et al., J. Dairy Research, "Partial purification and some properties of C2(W) lysin, a lytic enzyme produced by phage–infected cells of Streptoccus lactis C2", 52:123–138 (1985).
Garcia et al., J. Virology, "Cloning, Purification, and Biochemical Characterization of the Pneumococcal Bacteriophage Cp–1 Lysin", 61:2573–2580 (1987).
Raina, J. Bacteriology, "Purification of Streptococcus Group C Bacteriophage Lysin", 145:661–663 (1981).
Oram et al., Chemical Abstracts, "Phage–associated Lysins affecting group N and group D streptococci", 63:13631a (1965).
Erskine, Chemical Abstracts, "Effect of spermine on host–cell lysis and reproduction by a lactic streptococcal bacteriophage", 73:1175e (1970).
Shearman et al., Mol. Gen. Genet., "Cloning and DNA sequence analysis of a Lactococcus bacteriophage lysin gene", 218:214–221 (1989).

*Primary Examiner*—Donald E. Czaja
*Assistant Examiner*—Leslie Wong
*Attorney, Agent, or Firm*—Dickstein, Shapiro & Morin

[57] ABSTRACT

The lysin from a Lactococcus (preferably prolate-headed) bacteriophage is used to lyse bacterial starter cultures during cheese-making. Such bacteriophage include φvML3. In addition, the φvML3 lysin has been characterized and a coding sequence for it has been cloned.

4 Claims, 9 Drawing Sheets

```
          E  F  P  S  K  K  D  E  G  T  G  Y  A  F  R  K  D  G  Q  L  Y  V  G  S
GAATTCCCTAGTAAGAAAGACGAGGGAACTGGGTACGCCTTTAGAAAAGACGGACAATTATATGTCGGTTCC              72
EcoRI

I  K  A  Y  N  A  K  K  N  A  W  E  R  T  F  D  I  V  N  A  I  K  D  I
ATTAAAGCATATAACGCAAAGAAAAACGCGTGGGAACGTACTTTTGACATTGTGAACGCAATTAAAGATATC             144
                                                                  EcoRV

I  D  E  F  D  L  K  D  Y  H [M] A  I  E  T  P  I [M] G  R  N  R  K  H
ATAGATGAGTTTGACTTAAAAGACTATCACATGGCTATTGAAACGCCTATCATGGGTAGAAACAGAAAGCAC             216

S  I  T  L  A  N  C  N  G  Y  F  I  G  A  I  D  G  L  V  N  G  L  Y  F
AGTATCACATTGGCTAATTGTAACGGTTATTTTATCGGTGCTATTGACGGTCTAGTAAATGGCCTATACTTT             288

Y
TATTGATAACTCTAAATGGTGTAGCTATCATTTAATTTCAGGCAAACGAGAACAACGAAAAGAAGAAAGTTT             360
         5                1

GGAACTTTTAAAACAGACTGGACTTGTTCCGCTTGATTGTAAAGATGATAACATGGCTGACGCTTATAACAT             432
         DraI

TTTGACATATTGCGAACACTTGGGTTAGTTGTTCCCTTATAAAAAAACAATAATAATAATTGGAGGTGGTAA             504

TATAAAAGTATCACAAAACGGTTTGAACTTGATTAAAGAGT[TTGAGG]TTGTAGGTTGAC[TGC]TTATAA[ACC         576
                                                        HincII M  Y  T  I  G  W  G  H  Y  G  V  T  A  G  T  T  W  T  Q
TGTACCG[GGGAA]CAAATGTACACTATCGGTTGGGGTCATTATGGAGTGACAGCAGGTACAACATGGACACA             648
                                                2

A  Q  A  D  S  Q  L  E  I  D  I  N  N  K  Y  A  P  M  V  D  A  Y  V  K
AGCTCAAGCAGATAGCCAGCTAGAGATTGACATCAATAATAAGTATGCACCTATGGTTGACGCTTACGTAAA             720
                                                                  HincII
```

FIG.7A

```
       G  K  A  N  Q  N  E  F  D  A  L  V  S  L  A  Y  N  C  G  N  V  F  V  A
    AGGCAAAGCAAATCAAAATGAGTTTGACGCCTTAGTTTCATTGGCTTATAACTGTGGTAATGTTTTCGTTGC    792

D  G  W  A  P  F  S  H  A  Y  C  A  S  M  I  P  K  Y  R  N  A  G  G  Q
    TGACGGTTGGGCGCCTTTCTCACATGCTTATTGTGCTTCAATGATACCGAAGTATCGTAATGCAGGCGGTCA    864

V  L  Q  G  L  V  R  R  R  Q  A  E  L  N  L  F  N  K  P  V  S  S  N  S
    AGTCTTACAAGGCTTAGTAAGACGCAGACAGGCAGAGCTTAACTTATTTAATAAACCAGTATCAAGTAATTC    936
                                      ───────────────
                                             3

N  Q  N  N  Q  T  G  G  M  I  K  M  Y  L  I  I  G  L  D  N  S  G  K  A
    AAACCAAAACAATCAAACAGGAGGAATGATAAAAATGTACCTTATTATAGGACTAGATAATTCAGGTAAAGC   1008
                                                       ───────────────
                                                              4

K  H  W  Y  V  S  D  G  V  S  V  R  H  V  R  T  I  R  M  L  E  N  Y  Q
    TAAACATTGGTATGTTTCTGACGGTGTAAGTGTTCGTCATGTTCGTACAATTCGTATGTTGGAAAACTATCA   1080

N  K  W  A  K  L  N  L  P  V  D  T  N  V  Y  C  R  N  R  S  R  V  W  T
    AAACAAATGGGCTAAACTTAACTTGCCAGTTGATACCAATGTTTATTGCAGAAATCGAAGCAGAGTTTGGAC   1152

GTAAGATTGACATGGCTTCAGGAGAAGTGAAATAGGAGGAAGTGAATGAGGGAATC
                                                 EcoRI                          1209
```

FIG.7B

METHOD OF MAKING CHEESE USING VIRAL ENZYMES

This application is a continuation of international application PCT/GB 89/00791 filed on Jul. 12, 1989, now abandoned, which designated the United States.

The bacteriophage φvML3, which uses *Streptococcus lactis* MI3 as host, produces a bacteriophage lysin that causes distinct "halos" around viral plaques. This lysin is responsible for cell-wall degradation and lysis of the host cells. *Streptococcus lactis* has recently been renamed as *Lactococcus lactis* subsp. *lactis*.

The bacteriophage lysin of φvML3 has been partially purified and its ability to lyse bacteria other than *Lactococcus lactis* subsp. *lactis* ML3 has been investigated previously. The lysin was found to lyse strains of *Lactococcus lactis* subsp. *lactis* and subsp. *cremoris* and to have a weak effect on group D streptococci. Other bacterial genera tested were not affected [Oram. J. D. & Reiter, B. (1965) *J. Gen. Microbiol.* 40, 57–70; Reiter, B. & Oram, J. D. (1963) *J. Gen. Microbiol.* 32, 29–32].

The lysis of cheese-making bacteria by bacteriophages, or by other means, has previously been found to be a problem. We have now found that a substantially pure lysin enzyme can actually be used to advantage in the manufacture of cheese.

A first aspect of the invention provides a substantially pure preparation of the φvML3 lysin or a variant thereof, free of active said bacteriophage.

A second aspect of the invention provides a formulation comprising the lysin of a Lactoccus bacteriophage or a variant of such a lysin and suitable for addition to cheese or to a cheese precursor mixture. A formulation is suitable for addition to cheese or to a precursor if it does not immediately or later render the cheese unfit for consumption or prevent the formation of consumable cheese from the precursor mixture. The formulation is free of viable (active) bacteriophage. Preferably, the bacteriophage is a prolate-headed bacteriophage.

A third aspect of the invention provides a coding sequence for such a lysin, in isolation from the genes which would normally lie immediately upstream or immediately downstream of that gene in the associated bacteriophage, or a variant of such a coding sequence. A conservative variant is one in which the DNA sequence is different from that found naturally but, because of the degeneracy of the genetic code, encodes the same polypeptide fragments as does the nature-identical sequence. Other variants include coding sequences encoding polypeptides which have slightly different amino acid sequences from the lysin but which retain at least 10%, preferably at least 50%, 90%, 95% or 99% of the bacterial cell wall-degrading activity of the said lysin. Such activity may be measured by observing a change in optical density of a suspension of cells, for example *Lactoccus lactis* subsp. *lactis*, exposed to the lysin. Such variant polypeptides may include those which are slightly longer or shorter than the lysin or which have conservative amino acid substitutions. For example, a serine may be substituted for a threonine and vice versa and a glutamine may be substituted for an asparagine and vice versa. Generally, substitutions, deletions and additions at the N-terminus have less effect on function than at the C-terminus.

A fourth aspect provides a coding sequence as above in an expression vehicle suitable for transformation of a microbial host. The expression vehicle may have a control region for the coding sequence, the control region including a start codon upstream of the gene and the gene being in proper reading frame relative to the start codon or the expression vehicle may provide for insertion of the coding sequence into an endogenous heritable unit so that the coding sequence is under the control of such a control region therein. The control region may comprise the natural viral control region, a lactic streptococcal control region (such as the lactose operon) or other control regions which control, preferably inducibly, expression of the gene in the microbial host. For example, in *E. coli* one might use the lac control elements or those of the arabinose, colicine E1, galactose, alkaline phosphatase, tryptophan or lambda operons. In yeast (e.g. *Saccharomyces cerevisiae*), one might use the promoters for phosphoglycerokinase or for galactose.

Thus, a fifth aspect of the invention provides a microbial host transformed with such an expression vehicle and capable of expressing the lysin coding sequence. The microbial host may be any microorganism which is found to express the said lysin gene and may be a bacterium (such as *E. coli* or *Bacillus subtilis*), a fungus (such as *S. cerevisiae* or *Aspergillus nidulans*), a plant cell, a plant protoplast, or an animal cell. Preferably the host is *B. subtilis* or *Lactobacillus*.

Provided that the cell wall of the host is not itself degraded by the lysin, then the lysin-secreting transformed host may be useful in suppressing populations of bacteria which are susceptible to lysis by the lysin.

A sixth aspect provides a polypeptide derived from the expression of the said lysin coding sequence in a suitable microbial host transformed with such an expression vehicle. The invention also encompasses cloning vehicles comprising such coding sequences.

A seventh aspect provides a process for at least partially isolating the lysin gene from a prolate-headed bacteriophage by preparing from the DNA thereof the restriction fragment EcoRV-EcoRI of FIG. 7 or a corresponding fragment thereof, preferably in isolation from neighbouring bacteriophage sequences. (The EcoRI restriction site is actually created artificially by adding an EcoRI linker to an AluI site). The lysin gene of bacteriophages other than OVML3 can generally be obtained by identifying the bacterial cell wall lysing proteolytic enzyme thereof, sequencing it, creating a mRNA probe and isolating the gene, all in known ways.

An eighth aspect of the invention provides a method of making cheese comprising lysing the bacterial starter culture at a predetermined time during the preparation of the cheese by the addition of a Lactococcus bacteriophage lysin. Suitable starter culture bacteria include *Lactococcus lactis* subsp. lactis and cremoris. Preferably, the lysin is added at the end of the dairy fermentation such that the starter cells of the fermentation are lysed, thus releasing the intracellular enzymes. Some of these enzymes can then cause the mature flavour of cheese to develop and thus a method in accordance with the invention may be used to accelerate the maturation of the cheese. The lysin, at least in the quantities necessary, does not render the resulting cheese unfit for human consumption and may readily be removed from the cheese-making container or destroyed before the next starter culture is introduced.

A ninth aspect of the invention provides cheese made by such a process.

Prolate-headed bacteriophages include the following bacteriophages of *Lactococcus lactis*:

| Bacteriophage | Subspecies |
| --- | --- |
| c2 | lactis c2 |
| c6a | lactis c6 or c10 |
| c6B | lactis c6 or c10 |
| c6D | lactis c6 or c10 |
| C10I | lactis c10 |
| C10w | lactis c10 |
| drc1 | lactis DRC1 |
| 643 | lactis C8 |

Preferably, in all of the aspects of the invention discussed above, the lysin is the lysin from the bacteriophage φvML3. The bacteriophage is well known but, to avoid any possible doubt, we have deposited it at the National Collections of Industrial and Marine Bacteria. Aberdeen under the terms of the Budapest Treaty. The date of deposit was Jul. 5, 1989 and the accession number is NCIMB 40160.

We have similarly deposited the natural host of φvML3, namely *Lactococcus lactis* subsp. *lactis* ML3, on Jul. 5, 1989 as NCIMB 40161.

A person skilled in the art will readily be able to determine the most appropriate conditions of use of the lysin, for example the time of introduction of the lysin, the amount to be introduced, the nature of the composition being introduced and so on. These may vary according to the type of cheese being made. Generally, however, the lysin is added as a small volume (preferably no more than 5% or 1% of the volume of the cheese culture) of a sterile solution to give a concentration in the cheese fermentation culture of between 0.01 μg/l and 1500 mg/l. Or, the lysin may be encapsulated in liposomes (as in Kirby et al, (1987) Int. J. Food Sci. Tech. 22, 355–375) and added at the outset for delayed release.

Preferred embodiments of the invention will now be described by way of example and with reference to the accompanying drawings, in which:

FIG. 7 shows the total sequence of a 1.2 kilobase fragment of bacteriophage φvML3 DNA encoding the lysin gene which was cloned in λ.gt10-lysin 4, including the DNA sequence and deduced amino acid sequence for the bacteriophage lysin gene.

Figure 1A:
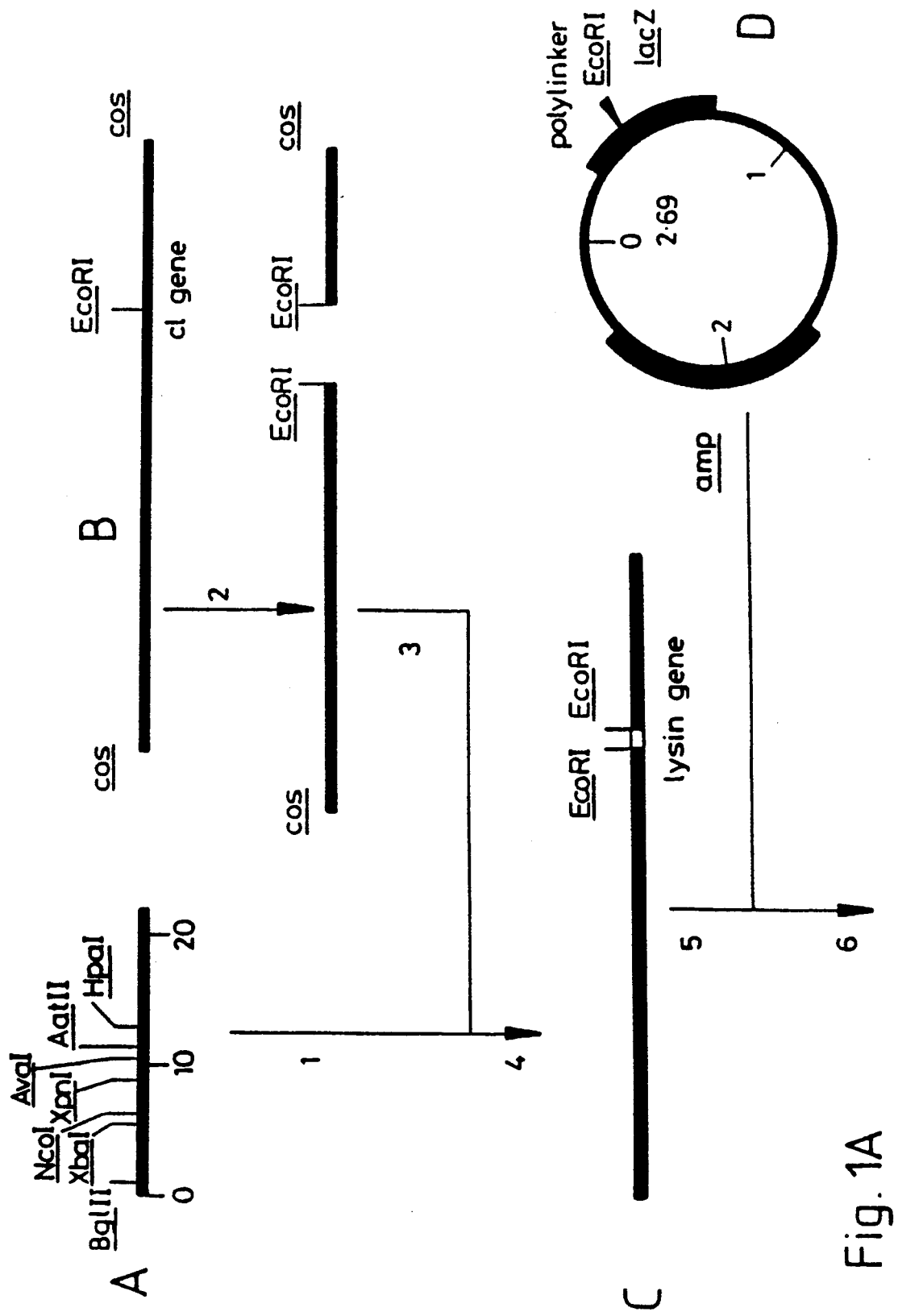
FIG. 1 (on two sheets) is a scheme of the stages in gene cloning used to isolate the φvML3 lysin gene.

EXAMPLE 1: CLONING OF LYSIN GENE ETC.

Preparation of bacteriophage φvML3 DNA

High titre bacteriophage OvML3 lysates were prepared by inoculating 500 ml of lactose M17 broth (Terzaghi & Sandine, 1975) with 2% of an overnight lactose M17 broth culture of *Lactococcus lactis* subsp. *lactis* ML3. This is freely available from the National Collection of Food Bacteria, Shinfield, Reading, Berks., U.K. The culture was grown to an O.D. 600 of 1.00±0.05 and 5 ml of 0.05M calcium borogluconate and 10 ml of φvML3 bacteriophage lysate with a concentration of $3.3 \times 10^{10}$ plaque-forming units per ml were added. φvML3 is also freely available from NCFB. Incubation was continued until complete lysis occurred and no further fall in optical density was observed (the optical density fell to an O.D. 600 of 0.34). Cell debris was removed by centrifugation at $8000 \times g$ for 15 minutes.

Bacteriophage were concentrated by centrifugation of the lysate at $125,000 \times g$ for 3 hours. The supernatant was discarded and the bacteriophage pellet was resuspended by storage overnight at 4° C. in 8 ml of a buffer consisting of 0.01M Tris hydrochloride, 0.1 mM EDTA, and 1 mM magnesium sulphate, pH 8.0.

The bacteriophage suspension was centrifuged at $1.600 \times g$ for 5 minutes and 4 ml of the supernatant was layered onto a stepped gradient prepared from 2 ml aliquots of caesium chloride solutions in buffer (as above), having specific gravities of 1.6, 1.5, 1.4 and 1.3. Gradients were centrifuged at $92,000 \times g$ for 2 hours at 5° C. in a swing-out centrifuge rotor. The band of bacteriophage formed was removed from the gradient with a small hypodermic syringe in a volume of approximately 0.5 ml and mixed with an equal volume of saturated caesium chloride solution in buffer (as above). This was placed at the bottom of a similar stepped gradient and centrifuged as before and once again the bacteriophage band was removed and placed in a 1.5 ml Eppendorf tube.

The high titre bacteriophage suspension was lysed to release the DNA by replacing the top of the Eppendorf tube with dialysis membrane, held in place with a tight rubber band, and performing dialysis for 18 hours at room temperature against 50% formamide in a buffer consisting of 0.1M Tris hydrochloride, 0.01M EDTA, pH 8.5. Formamide was removed by dialysis for 24 hours at 4° C. against a buffer consisting of 0.1M Tris hydrochloride, 0.1 mM EDTA, pH 7.5. The resultant bacteriophage DNA was purified by caesium chloride-ethidium bromide equilibrium density centrifugation for 60 hours at $125,000 \times g$. The DNA band was visualised under ultra-violet light and removed with a small hypodermic syringe. Ethidium bromide was extracted with caesium chloride saturated iso-amyl alcohol and caesium chloride was removed by dialysis for 24 hours at 4° C. against a buffer consisting of 0.1M Tris hydrochloride, 0.1 mM EDTA, pH 7.5.

Cloning the Bacteriophage φvML3 lysin gene

The bacteriphage φvML3 DNA was a 23.3 kilobase molecule with 3 recognition sites for restriction endonuclease EcoRI. A restriction map for the bacteriophage is shown in FIG. 1. Bacteriophage OvML3 DNA was partially digested with restriction endonuclease AluI in a reaction buffer to produce random blunt-ended DNA fragments. These were separated by electrophoresis at 4° C. in low-melting-point agarose (Sigma) and that region of separated DNA containing fragments in the size range 0.5 to 4.0 kilobases was cut from the gel. The agarose block was mixed with 5 volumes of a buffer consisting of 20 mM Tris hydrochloride, 1 mM EDTA, pH 8.0 and melted by heating to 65° C. for 5 minutes. At room temperature the DNA and agarose solution was successively extracted with equal volumes of phenol, phenol-chloroform and chloroform and the DNA was recovered by ethanol precipitation and resuspension in TE buffer. Eight base-pair phosphorylated linkers with the DNA sequence 5'-GGAATTCC-3' (Pharmacia), which includes the recognition site for restriction endonuclease EcoRI, were ligated to the purified blunt-ended fragments of bacteriophage φvML3 DNA. The ligation was performed overnight at 15° C. in a reaction mixture consisting of blunt-ended φvML3 DNA fragments, linker DNA and 5 units of DNA ligase enzyme (Boehringer Mannheim) in 50 ul of a buffer consisting of 70 mM Tris hydrochloride, 7 mM magnesium chloride, 0.07 mM ATP, pH 7.5. The reaction was stopped by incubation for 10 minutes at 65° C. and the linkers were trimmed by digestion at 37° C. for 2 hours with restriction endonuclease EcoRI in 100 ul of a buffer consisting of 100 mM Tris hydrochloride, 50 mM sodium chloride, 10 mM magnesium chloride, pH 7.5. The reaction was stopped by phenol extraction and the fragments of bacteriophage OvML3 were purified by chromatography over a NENSORB 20 column (DuPont).

Figure 2:
FIG. 2 is a photograph of vector λ.gt10 plaques and clones which express the lysin gene of bacteriophage φvML3.

Purified, EcoRI-digested and dephosphorylated DNA arms of bacteriophage lambda vector λ.gt10 were purchased from Northumbria Biologicals Ltd and ligated with pure DNA fragments of φvML3 DNA by incubation overnight at 4° C. with 1 unit of DNA ligase per 10 ul in a reaction buffer containing 50 mM Tris hydrochloride, 7 mM magnesium chloride, 1 mM dithiothreitol, 1 mM ATP, pH 8. Ligated DNA was packaged in vitro into lambda bacteriophage using crude cell-extracts prepared as described by Scalenghe et al. (1981) and Hohn (1979). Freeze-thaw lysates (FTL) were prepared from E. coli strain BHB2688 and sonic extracts from E. coli strain BHB 2690. The in vitro packaging reaction was carried out by the sequential addition of 350 ul buffer consisting of 20 mM Tris hydrochloride, 3 mM magnesium chloride, 0.05% β-mercaptoethanol, 1 uM EDTA, pH 8.0; 50 ul of ligated DNA; 50 ul of a buffer consisting of 30 mM spermine tri-hydrochloride pH 7.0, 30 mM putrescine-dihydrochloride pH 7.0, 18 mM magnesium chloride, 15 mM ATP, 1.2% β-mercaptoethanol; 175 ul of sonic extract (SE); 250 ul freeze-thaw extract (FTL). The mixture was incubated for 90 minutes at room temperature and 11.5 ml of lambda buffer consisting of 6 mM Tris hydrochloride, 10 mM magnesium chloride, 100 mM sodium chloride, 0.5 mg/ml gelatine, pH 8.0 was added, together with 50 ul of chloroform. The bacteriophage lambda suspension was plated on the E. coli host strain C600 hfl- using NZY agar plates. Lambda plaques that expressed the bacteriophage φvML3 lysin gene were detected by overlaying with a suspension of Lactococcus lactis subsp. cremoris NCDO 1196 cells in 0.1M potassium phosphate buffer pH 6.7 with 0.7% agarose. Plates were incubated at 30° C. for 6 hours and clones expressing bacteriphage OvML3 lysin produced a region of clearing above the lambda plaque as shown in FIG. 2. A collection of 50 clones, each expressing lysin, were purified by single-plaque isolation and retained. In FIG. 2, plaques of λ.gt10 with random cloned fragments of bacteriophage φvML3 DNA are shown. The plaques are overlayed with Lactoccus lactis subsp cremoris cells. Lambda clones which express a cloned lysin gene (arrowed) have produced a clear window in this lawn and appear dark, whereas other lambda plaques retain a cloudy appearance.

Characterisation of bacteriophage φvML3 lysin gene

One bacteriophage lambda clone that expressed the bacteriophage φvML3 lysin gene (λ.gt 10-lysin4) was characterised in detail. A large scale bacteriophage lambda lysate was prepared and DNA extracted as described above for bacteriophage φvML3. Digestion with restriction endonuclease EcoRI revealed the presence of a 1.2 kilobase DNA fragment from bacteriophage φvML3 which had cloned into the EcoRI site of lambda vector 2.gt 10.

Figure 3:
FIG. 3 is a photograph of an *E. coli* strain carrying the clone pFI106 which expresses bacteriophage φvML3 lysin.

This fragment was recloned into the EcoRI site of the E. coli plasmid vector pUC13. Vector DNA and λgt10-lysin 4 DNA were both digested with restriction endonuclease EcoRI, using a buffer consisting of 100 mM Tris hydrochloride, 50 mM sodium chloride, 10 mM magnesium chloride, pH 7.5. The reaction was stopped by phenol extraction and a mixture of the cleaved DNAs was incubated overnight at 15° C. with 1 unit of DNA ligase in a reaction buffer consisting of 50 mM Tris-hydrochloride, 7 mM magnesium chloride, 1 mM dithiothreitol, 1 mM ATP, pH 8. Ligated DNA was transformed into competent cells of E. coli strain TBI and ampicillin-resistant colonies were selected on B agar containing IPTG and "Bluogal" (BRL). Vectors with cloned DNA were identified by their white colour. Their ability to produce bacteriophage φvML3 lysin was tested by overlaying colonies with a suspension of Lactococcus lactis subscp. cremoris NCDO 1196 cells in 0.1M potassion phosphate buffer, pH 6.7, with 0.7% agarose. Zones of clearing, as illustrated in FIG. 3, for one isolated clone were detected. (In FIG. 3, colonies Escherichia coli carrying plasmid pFI 106 are overlayed with Lactococcus lactis subsp. cremoris cells. Expression of lysin causes a clear zone of lysin in the cloudy lawn of Lactococcus cells.) The plasmid from this clone named pFI106 was isolated and analysed by restriction endonuclease mapping. It had the structure shown in FIG. 4.

Figure 4:
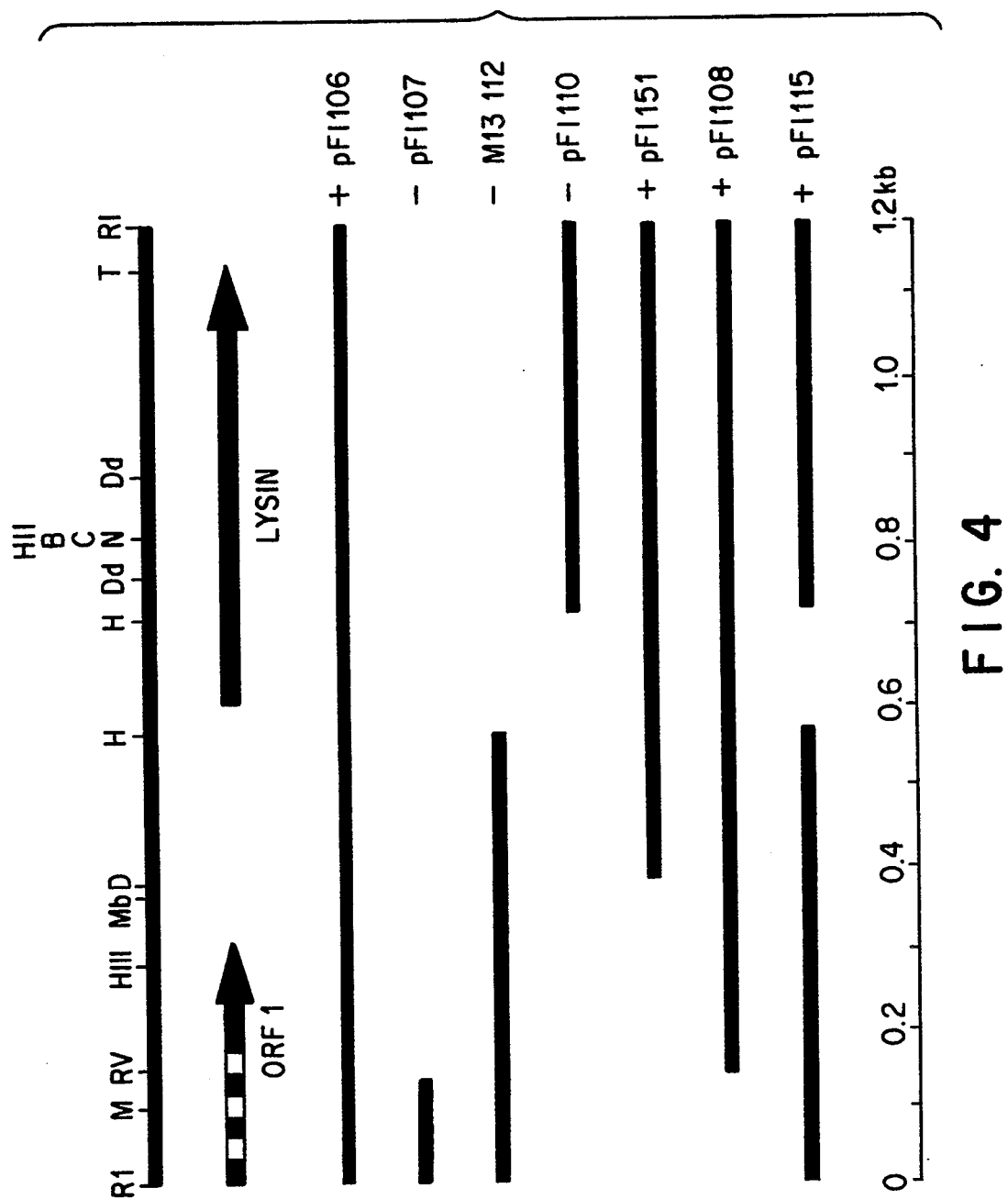
FIG. 4 is a restriction and deletion map of a fragment of bacteriophage φvML3 encoding the lysin gene.

In FIG. 4, the independently determined restriction map is confirmed by data derived from the DNA sequence. (RI: EcoRI: M: MluI: RV: EcoRV; HII: HaeII; Mb: MboII; D: DraI; H: HincII; Dd: DdeI; HIII: HaeIII; B: BanI; C: CfoI; N: NarI; T: TaqI) The precise locations of the lysin gene and ORF1 are deduced from the sequence analysis. The broken line for ORF1 indicates its possible extension upstream of methionine residues detected by sequence analysis. In the deletion analysis, regions of DNA retained in sub-clones are indicated by solid bars. The presence or absence of lysin activity in these constructs is indicated by + or −.

The 1.2 kilobase fragment of bacteriophage φvML3 DNA that expressed lysin activity was recloned using the strategy described above for vector pUC13 but into lactic streptococcal vectors pCK1, pCK536 and pTG262. Clones were selected by their resistance to chloramphenicol and detected by their ability to produce lysin when overlaid with Lactococcus lactis subsp. cremoris NCDO 1196 cells as described above. Examples of constructed clones consisting of lactic streptococcal vectors able to express the lysin gene of bacteriophage OvML3 are shown in FIG. 1.

From pFI106 a series of deleted derivatives of the cloned 1.2 kilobase fragment of bacteriphage OvML3 DNA were made using restriction endonuclease digestion and either re-ligation or recloning into another vector. The details of construction and the structure of these derivatives are shown in FIG. 4. All of the derivatives were tested for their ability to produce bacteriophage φvML3 lysin and the results are also shown in FIG. 4. From the results it was possible to define the region of bacteriophage φvML3 that encodes the lysin gene. It is between coordinate 0.37 (DraI site) and coordinate 1.2 (EcoRI site) of the restriction endonuclease map shown in FIG. 4. The region of DNA between coordinate 0.565 (HincII site) and coordinate 0.71 (HincII site) is essential for the expression of lysin and this region is deleted in derivative plasmid pFI115 as shown in FIG. 4.

Figure 5:
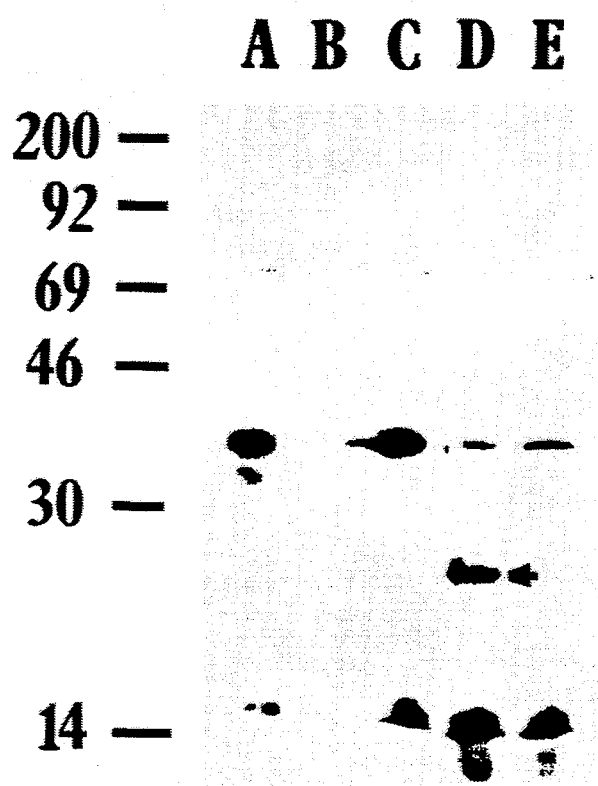
FIG. 5 is a fluorograph of proteins expressed by pUC13 plasmid vector DNA, by plasmid pFI106 which expresses lysin and by plasmid pFI115 which does not express lysin.

The proteins encoded by plasmid pFI106, which expresses the bacteriophage φvML3 lysin, and the derivative plasmid pFI115, which does not express lysin, were compared using the in vitro transcription and translation technique. Radioactively labelled $^{35}$S L-methionine was incorporated into proteins expressed by these plasmid DNAs using the reagents and methodology of a commercial kit (Amersham). Radio-labelled proteins that were expressed were separated by SDS polyacrylamide gel electrophoresis and detected by fluorography. As shown in FIG. 5, plasmid pFI106 expressed a protein of 23 kilodaltons which was not expressed by either the vector pUC13 or by the deleted derivative plasmid pFI115. The lysin enzyme of bacteriophage OvML3 is shown to be a protein of 23 kilodaltons.

In FIG. 5, the fluorograph is of radioactively labelled proteins expressed by plasmid vectors and clones during in vitro transcription/translation and separated by SDS polyacrylamide gel electrophoresis. $^{35}$S-labelled proteins expressed by pAT153 control DNA (lane A); no DNA (lane B); pUC19 vector DNA (lane C), pFI106 DNA which expresses cloned lysin (lane D), pFI115 DNA in which part of the lysin gene is deleted (lane E) are shown. Protein molecular weight standards labelled with $^{14}$C are shown to the left.

Figure 6:
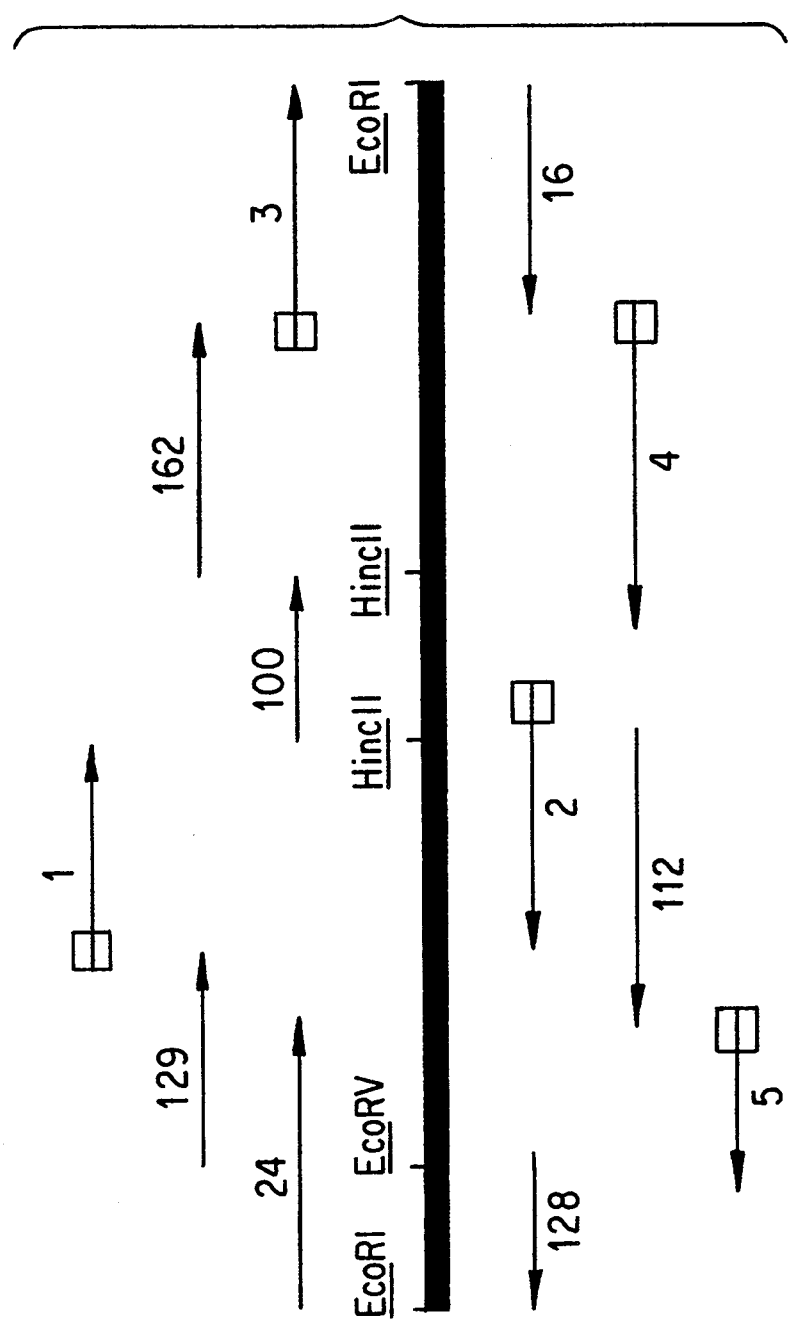
FIG. 6 is a scheme showing the DNA sequencing strategy used.

Referring to FIG. 6, the 1.2 kilobase EcoRI fragment containing the φvML3 lysin gene and derivative fragments were cloned into M13mp18. The clones were used as a source of DNA templates for DNA sequence determination by the Sanger dideoxy chain termination method. DNA sequences determined are indicated by the direction and extent of the arrows. Sequences indicated by boxed arrows were primed by synthetic oligonucleotides designed from already determined sequence data. These synthetic primers are also indicated in FIG. 6.

In addition to sequences determined by initiation from M13 DNA, using commercially available M13 primers, a number of synthetic primers were made from φvML3 DNA sequences that had already been determined. These are also shown in FIG. 7. The complete DNA sequence for both strands of the 1.2 kilobase DNA fragment of bacteriophage φvML3 was determined. This is presented in FIG. 7. The sequence was analysed using the Staden "Analseq" programme, which revealed an open reading frame consistent with the location of the lysin gene as revealed by deletion mapping and lysin expression determination (FIG. 4) and with the molecular weight of the lysin enzyme determined by in vitro transcription and translation of plasmids pFI106 and pFI115. The DNA sequence for the lysin gene of bacteriophage OvML3 and its deduced amino-acid sequence are shown in FIG. 7.

Referring to FIG. 7, restriction endonuclease sites used in the construction of M13mp18 clones for sequence determination are indicated. Solid lines show the synthetic primers that were used in the sequencing strategy (FIG. 4). Primers 1 and 3 were as shown, whereas primers 2, 4 and 5 were the complementary sequence. The lysin structural gene is located between positions 593 and 1153. Its amino-acid sequence and that of ORF1 are shown. For ORF1 in-frame methionine residues are boxed. The possible lactic streptococcal promoter (position 550 to 580) and ribosome binding site (position 585) for the lysin gene are also boxed.

EXAMPLE 2: MODEL CHEESE-MAKING PROCESS

Starter cell lysis by cloned bacteriophage lysin

An *E. coli* strain carrying plasmid pFI106 was grown to stationary phase in L-broth and washed and resuspended in a one-tenth volume of a buffer consisting of 0.1M potassium phosphate, pH 6.7. Cells were broken by four 30-second bursts of ultrasonication using an MSE ultrasonicator. Cell debris was removed by centrifugation for 30 minutes at 4° C. and 20,000 x g.

The supernatant was used as a crude lysin preparation. A negative control was prepared in the same way from an *E. coli* strain carrying plasmid pFI115, which does not express bacteriophage φvML3 lysin. Subspecies *cremoris* cells suspended in a buffer consisting of 0.1M potassium phosphate, pH 6.7, were rapidly lysed by the crude lysin preparation: with lysin, the $OD_{600}$ fell from 1.2 to 0.19 in 7 minutes, whereas without lysin the $OD_{600}$ fell only to about 1.19. A Subspecies *cremoris* cheese starter strain was grown in milk for 6 hours in an experiment that modelled a dairy fermentation. Crude lysin preparation, a similar preparation from the negative control and buffer were added to three separate aliquots of the fermented milk and stored at 4° C. The viable count of subspecies *cremoris* cells was monitored and, as shown in Table 1 a rapid loss of viable cells due to lysis was observed in the milk fermentation treated with crude lysin preparation but not in the negative control or buffer experiments.

TABLE 1

A 6-HOUR MILK FERMENTATION USING *LACTOCOCCUS LACTIS* SUBSP. *CREMORIS* NCDO 1196 STARTER
(Starting Viable Count 3.45 × 10$^9$)

| | Viable Count | | | % Viability | | |
|---|---|---|---|---|---|---|
| | 24 h | 48 h | 72 h | 24 h | 48 h | 72 h |
| No addition | 2.9 × 10$^9$ | 2.8 × 10$^9$ | 1.6 × 10$^9$ | 81 | 81 | 46 |
| Extract of lysin-producing clone | 1.5 × 10$^6$ | 1.5 × 10$^6$ | 1.3 × 10$^5$ | 0.04 | 0.01 | 0.04 |
| Extract of lysin-negative control | 3.0 × 10$^9$ | 3.3 × 10$^9$ | 1.5 × 10$^9$ | 87 | 96 | 44 |

EXAMPLE 3: PREPARATION OF LYSIN COMPOSITION FOR CHEESEMAKING

A bacterial culture which expresses the bacteriophage lysin (e.g. *E.coli* carrying plasmid pFI106) is grown overnight in broth. A culture (400 ml) is centrifuged and the cells resuspended in a one tenth volume of TE buffer. Lysin is released from the cells, e.g. by chloroform addition and centrifugation. The lysin-rich supernatant is precipitated with 45% ammonium sulphate and the pellet resuspended in 3 ml of 0.1 m potassium phosphate buffer pH6.7 and passed through a PD10 column to desalt the sample. Further purification was by F.P.L.C. using an anion exchange column and a Sepharose 6 gel filtration column.

EXAMPLE 4: USE OF BACTERIOPHAGE LYSIN IN CHEDDAR CHEESEMAKING

A conventional manufacturing process for cheddar cheese is followed. After milling and salting, a preparation of cloned bacteriophage lysin is added. The incorporated lysin ensures early lysis of the starter culture and accelerates cheese maturation by the release of a flavour generating cocktail of starter enzymes.

An alternative is to encapsulate the lysin so that the timing of its addition is not important. The encapsulating agent dissolves after the cheese-making process is complete thus not affecting the starter bacteria before their role in acidification was complete.

References

Hohn, B. (1979) *Methods in Enzymology*. (ed., R. Wu)., vol. 68, 299–309.

Scalenghe, F., Turco, E., Edstrom, J. E. Pirrotta, V. & Melli, M. (1981). Chromosoma 32, 205–216.

Terzaghi, B. K. & Sandine, N. E. (1975). *Applied Microbiology* 29, 807–813.

Figure 1B:
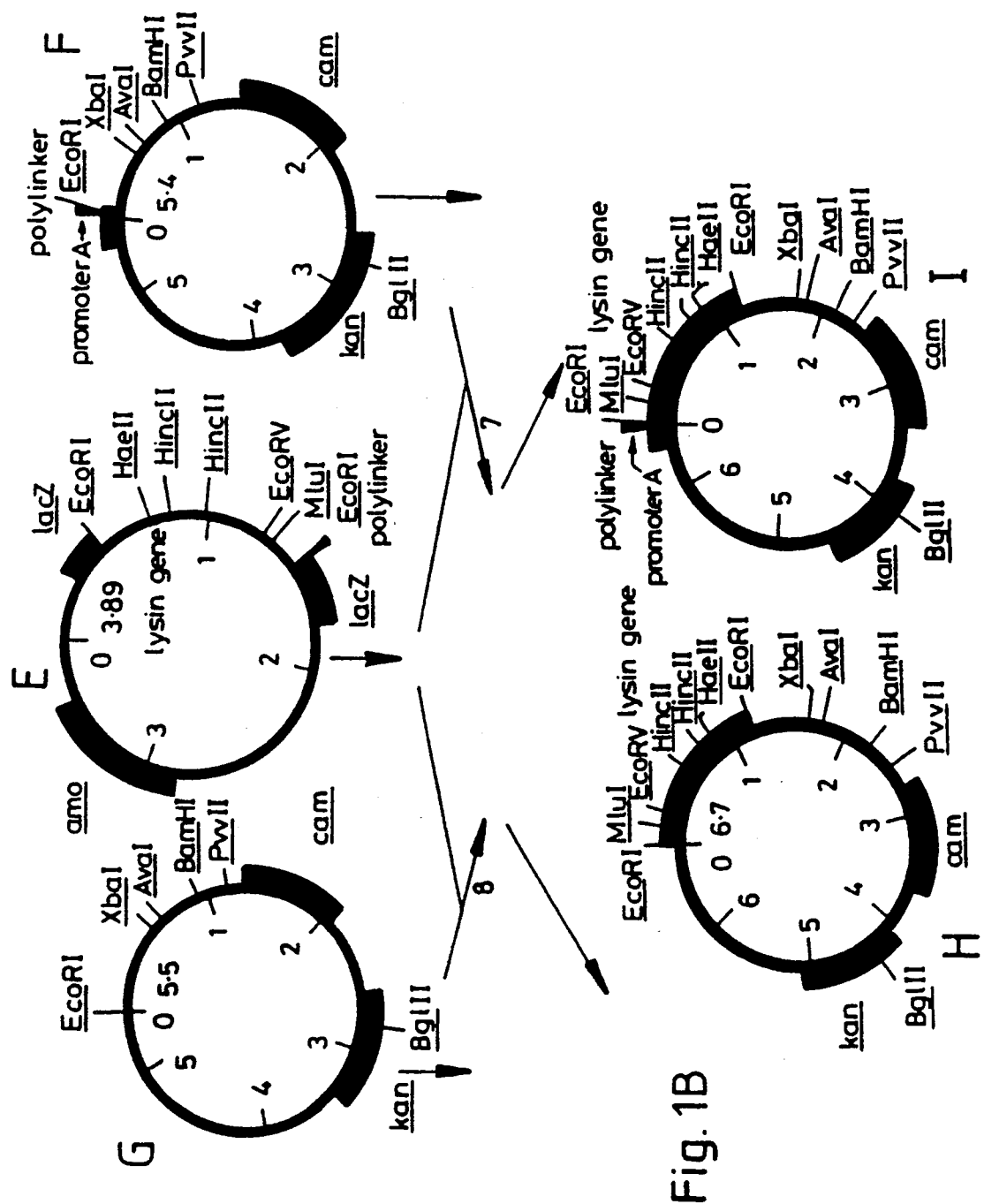

Key to FIGS. 1A and 1B

FIG. 1A: A is a restriction map of φvML3 which, at arrow 1, is partially AluI-digested. Blunt-ended fragments of 0.5–4.0 Kb are isolated, ligated with EcoR1 linkers and trimmed by digestion with EcoR1.

B is a map of vector lambda.gt 10, arrow 2 representing EcoR1 digestion and dephosphorylation thereof to lambda.gt 10 arms. At arrow 3, the product is ligated, packaged in vitro into lambda phage and plated onto *E.Coli* C6000 hfl− for lysin production detection. In step 4, the products of steps 1 and 3 are combined to form a lysin-producing clone lambda gt.10-lysin 4, shown at C. This is digested (5) with EcoR1 and ligated (6) with EcoR1-digested and dephosphorylated vector pUC13, shown at D. The product is transformed into *E.Coli* TB1 using agar with ampicillin, IPTG and Bluogal. White colonies producing lysin are selected.

FIG. 1B: Clone pFI106 (E) is digested with EcoR1 and ligated (7) with EcoR1-digested lactic streptococcal vector pCK536 (shown at F) and (8) with EcoR1-digested vector pCK1 (at G). *E.coli* 1106 is transformed with the products of steps 7 and 8, chloramphenicol-resistant colonies are selected and two ampicillin-sensitive lysin producing clones are obtained, pFI136 (shown at H) and pFI137 (at I).

I claim:

1. In a method of making cheese the improvement comprising the step of lysing a bacterial starter culture with a lysin of a Lactococcus bacteriophage or a variant of such a lysin which retains at least 10% of bacterial cell wall degrading activity of said lysin, wherein said lysin is suitable for addition to cheese or to a cheese precursor mixture and is free of active said bacteriophage.

2. A method according to claim 1 wherein the bacteriophage is a prolate-headed bacteriophage.

3. A method according to claim 2 wherein the bacteriophage is φvML3.

4. A method according to any one of claims 1 to 3 wherein the method comprises the step of dairy fermentation and the lysin is added at the end of the dairy fermentation.

* * * * *